(12) United States Patent
Stenqvist

(10) Patent No.: US 7,465,275 B2
(45) Date of Patent: Dec. 16, 2008

(54) METHOD AND APPARATUS FOR MEASURING FUNCTIONAL RESIDUAL CAPACITY (FRC) AND CARDIAC OUTPUT(CO)

(75) Inventor: Ola Stenqvist, Viken (SE)

(73) Assignee: GE Healthcare Finland Oy (FI)

( * ) Notice: Subject to any disclaimer, the term of this patent is extended or adjusted under 35 U.S.C. 154(b) by 889 days.

(21) Appl. No.: 10/479,390

(22) PCT Filed: May 29, 2002

(86) PCT No.: PCT/SE02/01019

§ 371 (c)(1),
(2), (4) Date: Jul. 22, 2004

(87) PCT Pub. No.: WO02/096289

PCT Pub. Date: Dec. 5, 2002

(65) Prior Publication Data

US 2004/0249301 A1    Dec. 9, 2004

(30) Foreign Application Priority Data

May 29, 2001   (SE)   .................................. 0101912

(51) Int. Cl.
*A61B 5/02* (2006.01)
*G01N 1/22* (2006.01)
*G01N 31/00* (2006.01)
*G01N 33/497* (2006.01)

(52) U.S. Cl. ........................... 600/532; 73/23.3; 422/84
(58) Field of Classification Search ....................... None
See application file for complete search history.

(56) References Cited

FOREIGN PATENT DOCUMENTS

| EP | 0392503 | 10/1990 |
|---|---|---|
| WO | 99/25244 | 5/1999 |
| WO | 00/67634 | 11/2000 |

OTHER PUBLICATIONS

*Measurement of Lung Volume by Sulfur Hexafluoride Washout during Spontaneous and Controlled Ventilation: Further Development of a Method*, A. Larsson et al., Anesthesiology 67:543-550, 1987.
*Automated sulfur hexafluoride washout functional residual capacity measurement system for any mode of mechanical ventilation as well as spontaneous respiration*, Thomas D. East, PhD et al., Critcal Care Medicine, vol. 18, No. 1, 1990.
*Perioperative functional residual capacity*, R. W. M. Wahba MB BCh MSc(McGill) FRCPC; Can J. Anaesth 1991, 38:3, pp. 384-400.

(Continued)

*Primary Examiner*—Robert L Nasser
(74) *Attorney, Agent, or Firm*—Andrus, Sceales, Starke & Sawall, LLP

(57) ABSTRACT

The present invention relates to a method and an apparatus for measuring Functional Residual Capacity (CO). Further, it relates to a method and an apparatus for measuring cardiac output (CO). The method comprises the steps of determining the amount of oxygen and carbon dioxide being inhaled and exhaled during at least two breathing cycles, identifying at least one difference between said breathing cycles, and estimating the FRC and/or CO based on the determined uptake of oxygen and excretion of carbon dioxide and said identified difference.

52 Claims, 5 Drawing Sheets

OTHER PUBLICATIONS

*A simple method to estimate functional residual capacity in mechanically ventilated patients*, R. Fretschner et al., Intensive Care Med (1993) 19:372-376.

*Continuous non-invasive monitoring of energy expenditure, oxygen consumption and alveolar ventilation during controlled ventilation: validation in an oxygen consuming lung model*, K. Holk et al., Acta Anaesthesiol. Scand. 1996: 40, p. 539-537.

*A deep breath method for noninvasive estimation of cardipulmonary parameters*, Richard R. Mitchell, International Journal of Clinical Monitoring and Computing, 5:53-64, 1988.

*Cardiopulmonary monitoring in the respiratory intensive care unit*, John J. Osborn, M.D., Cardiopulmonary Monitoring in the Respiratory ICU, Medical Instrumentation, vol. 11, No. 5, Sep.-Oct. 1977, pp. 278-282.

METHOD AND APPARATUS FOR MEASURING FUNCTIONAL RESIDUAL CAPACITY (FRC) AND CARDIAC OUTPUT(CO)

CROSS REFERENCE TO RELATED APPLICATION

The present application is the U.S. national stage application of International Application PCT/SE02/01019, filed May 29, 2002, which international application was published on Dec. 5, 2002 as International Publication WO 02/096289. The International Application claims priority of Swedish Patent Application 0101912-4, filed May 29, 2001.

FIELD OF THE INVENTION

The present invention relates to a method and an apparatus for measuring Functional Residual Capacity (FRC). Further, it relates to a method and an apparatus for measuring cardiac output (CO).

BACKGROUND OF THE INVENTION

For both diagnostic and therapeutic it is important to determine lung volume, its subdivisions, and divergence of volumes from normal. The diagram in FIG. 1 shows the changes in volume (on the vertical axis) against time (on the horizontal axis) as an individual breath, initially tidal volumes, and then inspires and expires maximally. As is clearly illustrated, the Total Lung Capacity (TLC) comprises a Vital Capacity (VC) and a Residual Volume (RV). The Vital Capacity could be measured with spirometry, and comprises a Tidal Volume (TV), an Expiratory Reserve Volume (ERV) and an Inspiratory Reserve Volume (IRV). The Expiratory Reserve Volume in combination with the Residual Volume is denominated as Functional Residual Capacity (FRC).

Perhaps the volume that has received most attention is the Functional Residual Capacity (FRC), the volume of gas in the lung after a normal expiration. The FRC is determined by the balance between the inward elastic recoil of the lungs and the outward recoil of the thoracic cage. FRC decreases with paralysis and anaesthesia. Other factors influencing the FRC include:
  Body size
  Gender
  Posture
  Lung pathology.

Accordingly, it is in many cases important to estimate and/or monitor the Functional Residual Capacity (FRC). Even though this is important for patients with spontaneous breathing, it is most important in ventilator treated patients as FRC is involved in gas exchange and ventilation/perfusion ratio and may be used as an indicator of atelectases. In intubated patients FRC may also be manipulated by Positive End Expiratory Pressure (PEEP) level in order to avoid cyclic collapse of lung as part of a protective ventilatory strategy. The PEEP should be held at a level high enough to avoid cyclic collapse of the lung, but low enough to avoid overdistension of the lung.

However, conventional spirometry cannot provide any of the volumes that include RV, the residual volume left in the lung after maximal expiration. Other methods are therefore required to find FRC. Methods used in the intensive care unit (ICU) for FRC monitoring are based on dilution of a bolus of low solubility gas or long term sampling of expiratory gas. However, these methods require expensive mass spectroscopy or calibrated infrared and acoustic detectors and are therefore of limited clinical use. Other methods are based on a step-change in nitrogen concentration, such as a change in inspired oxygen concentration by more than 30% nifo, which may not be feasible in a patient with accute respiration failure. Such known methods are e.g. disclosed and discussed in:

Larsson A, Linnarsson D, Jonmarker C, Jonson B, Larsson H, Werner O (1987): "Measurement of Lung Volume by Sulfur Hexafluoride Washout during Spontaneous and Controlled Ventilation: Further Development of a Method", Anesthesiology 67:543-550

East T D, Wortelboer P J M, van Ark E, Bloem F H, Peng L, Pace N L, Crapo R O, Drews D, Clemmer T P (1990): "Automated sulfur hexafluoride washout functional residual capacity measurement system for any mode of mechanical ventilation as well as spontaneous respiration", Crit. Care Med 18(1):84-91

Wahba RWM (1991): "Perioperative functional residual capacity", Can J Anaesth 38(3):384-400

Fretschner R, Deusch H, Weitnauer A, Brunner JX (1993): "A simple method to estimate functional residual capacity in mechanically ventilated patients", Intensive Care Med 19:372-376

However, a common problem with all the known methods for estimation of FRC are that they are difficult, complex and expensive to use. Moreover, they can e.g. not be used for continuous monitoring with repeated measurements, and they are often unreliable. Accordingly, FRC is a parameter which is very difficult to determine and to monitor, especially in patients with acute respiratory failure. It is also important to monitor FRC in other conditions, since a reduction of FRC frequently indicates an early stage of disease and may assist in the identification of a patient which will subsequently need respirator or ventilator treatment. However, ventilator treatment is very expensive and may require the resources of an intensive care unit. It is therefore important to identify such patients at an early stage, whereby preventive measures, such as CPAP-ventilation, could be taken in order to reduce the number of prospective ventilator/respirator users.

In a patient which requires a ventilator, restoration of the FRC is an important measure. FRC may be restored by application of an enhanced end expiratory pressure. However, today there is no clinically usable objective method for measuring FRC.

In many types of pulmonary (lung) diseases it is also important to follow (monitor) the development of FRC over time, for diagnostic and therapeutic reasons.

For non-ventilator patients, there is still a need for adequate and reliable measurement of FRC. Today, a body plethysmograph is used which is not easy to use, nor to move around.

Another physiological variable which is difficult to measure and monitor is Cardiac Output (CO). A current and most frequently used method is based on invasive application of a pulmonary catheter with thermal dilution technique. However, this method is complex, expensive, and difficult to use. Still further, the methodological procedure contains a considerable health risk for the patient. Thus, the method is currently only used in severe cases in intensive care, even though the clinical need for reliable CO measurements is considerably higher. In particular, there is frequently a need for continuous monitoring of CO, which is today not achievable.

A reliable CO measurement is also important for healthy persons and persons with spontaneous respiration, and not only for diagnostic purposes in medical attendance. For example, there is a need for CO measurement for individuals undergoing exercise and physical capacity tests or evaluations.

OBJECTS OF THE INVENTION

It is therefore a first object of the present invention to provide a method and an apparatus for measuring Functional Residual Capacity (FRC), which at least alleviates the above-discussed problems experienced in the prior art. Further, it is a second object of the present invention to provide a method and an apparatus for measuring cardiac output (CO), which at least alleviates the above-discussed problems experienced in the art.

These objects are achieved by the invention as defined in the appended claims.

SUMMARY OF INVENTION

The present invention discloses a method and a corresponding apparatus for determining FRC based on a measured decrease in end-tidal alveolar oxygen concentration due to a known wash out of oxygen from the FRC during a short apnea or other suitable change in ventilation pattern. That is, the washed in volume of oxygen divided by the oxygen concentration difference gives the FRC.

Strictly speaking this relationship only holds if the FRC does not change during the apnea. In reality the FRC actually changes, i.e, decreases during apnea by a volume equivalent to the washed out volume of oxygen. However, during the same apnea period, there is also a wash in to the FRC of carbon dioxide that counteracts the decrease of the FRC volume caused by the wash out of oxygen.

The wash in volume of carbon dioxide is dependent on the metabolic production of carbon dioxide, the volume of FRC, and the amount of blood perfusing the FRC during the apnea, i.e., the cardiac output. Thus, the decrease in oxygen concentration in the FRC during the apnea is dependent on the metabolic uptake of oxygen from the FRC (the oxygen washed out of the FRC during the apnea), the FRC as such, and the carbon dioxide metabolically produced which, in part, is washed into the FRC during the apnea and, in part, remains in the lung capillary blood and passes over to the left heart without being washed out into the FRC. The latter part of the metabolically produced carbon dioxide, the lung capillary blood carbon dioxide, $LCBCO_2$, is dependent on the cardiac output and the increase in carbon dioxide concentration of the FRC during the apnea, which is dependent on the volume of the FRC.

In consequence, the determination of FRC from oxygen concentration changes during an apnea requires the measurement of the metabolic uptake of oxygen and the determination of $LCBCO_2$ which, in turn, is based on the measurement of metabolically produced carbon dioxide. Thus, a prerequisite of the invention is the simultaneous measurement of oxygen and carbon dioxide metabolic fluxes and concentration changes during the apnea since the oxygen and carbon dioxide fluxes and concentrations dependent on each other, as well as the volume of FRC and the cardiac output.

The present invention also discloses a method and a corresponding apparatus for determining lung capillary perfusion—cardiac output—based on measured changes in end-tidal alveolar FRC carbon dioxide concentration as a result of a short apnea or other suitable change in ventilation pattern. The increase in end-tidal carbon dioxide concentration is dependent on the metabolic output of carbon dioxide, how much of the metabolically produced carbon dioxide that will remain in lung capillary blood as a result of the increase in FRC carbon dioxide concentration which is dependent on the cardiac output and the volume of the FRC. The metabolic output of carbon dioxide prior to the apnea is easily measured with conventional indirect calorimetric methodology. The volume of FRC can be calculated based on a measured decrease in end-tidal alveolar oxygen concentration due to a known wash out of oxygen from the FRC during the apnea or other change of the ventilation pattern; i.e., the washed in volume of oxygen divided by the oxygen concentration difference gives the FRC volume.

As mentioned above this relationship, strictly speaking, only holds if the FRC does not change during the apnea. In reality the FRC actually changes, i.e, decreases, during apnea by a volume equivalent to the washed out volume of oxygen. However, during the same apnea period, there is also a wash in to the FRC of carbon dioxide that counteracts the decrease of the FRC caused by the wash out of oxygen. The wash in volume of carbon dioxide is dependent on the metabolic production of carbon dioxide, the FRC as such, and the amount of blood perfusing the FRC/lung interface during the apnea, i.e., the cardiac output. Thus, the decrease in oxygen concentration in the FRC during the apnea is dependent on the metabolic uptake of oxygen from the FRC (the oxygen washed out of the FRC during the apnea), the FRC as such, and the carbon dioxide metabolically produced which, in part, is washed into the FRC during the apnea and, in part, remains in the lung capillary blood and passes over to the left heart without being washed out into the FRC.

The latter part of the metabolically produced carbon dioxide, $LCBCO_2$, is dependent on the cardiac output and the increase in carbon dioxide concentration of the FRC during the apnea, which is dependent on the volume of the FRC. In consequence the determination of cardiac output from oxygen concentration changes during an apnea requires the measurement of the metabolic uptake of oxygen and the determination of $LCBCO_2$ which, in turn, is based on the measurement of metabolically produced carbon dioxide. Thus, a prerequisite of the invention is the simultaneous measurement of oxygen and carbon dioxide metabolic fluxes and concentration changes during the apnea since the oxygen and carbon dioxide fluxes and concentrations dependent on each other, as well as the volume of FRC and the cardiac output.

The aforementioned change in ventilation pattern can be a short apnea but also, for instance, a substantially smaller or larger breath of known volume than the preceding breaths. Such changes in ventilation pattern will cause a change of the FRC oxygen and carbon dioxide concentrations on which the calculation of the FRC volume as well as the cardiac output is based. Thus any well defined change in the breathing pattern capable of causing a measurable change in FRC oxygen and carbon dioxide concentrations can be used for calculation of the volume of FRC and cardiac output. A change in breathing pattern affecting respiratory gas concentrations can be followed by providing a compensatory change in an opposite direction in order to rapidly re-establish steady state conditions whereby a new measurement may be carried out with a minimal delay. Thus, an apnea following a breath with, for instance, twice the normal volume can be used. If a large breath is used to disturb the equilibrium it can be followed by a small breath, and vice versa. The effect on gas concentrations of the compensatory breath may be utilised to further improve calculations of FRC and cardiac output.

The method of the invention for estimation of functional residual capacity (FRC) in a person comprises establishing a breathing pattern; determining the amount of oxygen and carbon dioxide being inhaled and exhaled during a first breathing cycle comprised by said breathing pattern; accomplishing a first change in said breathing pattern of known magnitude; determining the amount of oxygen and carbon dioxide being inhaled and exhaled during a second breathing cycle; and estimating the FRC based on the determined amount of oxygen and carbon dioxide in said first and second breathing cycles.

The apparatus of the invention for measuring functional residual capacity (FRC) comprises means for establishing a breathing pattern; means for determining the amount of oxygen and carbon dioxide being inhaled and exhaled during a first breathing cycle comprised by said breathing pattern; means for accomplishing a first change in said breathing pattern of known magnitude; means for determining the amount of oxygen and carbon dioxide being inhaled and exhaled during a second breathing cycle; and means for estimating the FRC based on the determined amount of oxygen and carbon dioxide in said first and second breathing cycles.

The method of the invention for estimation of cardiac output (CO) in a person comprises establishing a breathing pattern; determining the amount of oxygen and carbon dioxide being inhaled and exhaled during a first breathing cycle comprised by said breathing pattern; accomplishing a first change in said breathing pattern of known magnitude; determining the amount of oxygen and carbon dioxide being inhaled and exhaled during a second breathing cycle; and estimating the CO based on the determined amount of oxygen and carbon dioxide in said first and second breathing cycles.

The apparatus of the invention for measuring cardiac output (CO)-comprises means for establishing a breathing pattern; means for determining the amount of oxygen and carbon dioxide being inhaled and exhaled during a first breathing cycle comprised by said breathing pattern; means for accomplishing a first change in said breathing pattern of known magnitude; means for determining the amount of oxygen and carbon dioxide being inhaled and exhaled during a second breathing cycle; and means for estimating the CO based on the determined amount of oxygen and carbon dioxide in said first and second breathing cycles.

According to an aspect of the invention, a method for estimation of functional residual capacity (FRC) comprises the steps of determining the amount of oxygen and carbon dioxide being inhaled and exhaled during at least two breathing cycles, identifying at least one difference between said breathing cycles, and estimating the FRC based on the determined amount of oxygen and carbon dioxide and said identified difference.

The inventive method is based on the on the surprising clinical observation made by the present inventor, that patients with low FRC and high oxygen consumption desaturate rapidly compared to "normal" patients. The method is simple and inexpensive to use, since no additional gases or the like are used. Instead, the estimation is made during relatively normal conditions for the patient. Still, the method has shown to be surprisingly reliable.

Further, the method may be used for relatively continuous monitoring of FRC, i.e. where repeated measurements are performed over a time period. This makes it possible to use the FRC measurements for diagnostic and routine control purposes, whereby e.g. lung diseases could be discovered well before they enter into severe phases.

Amount of oxygen and carbon dioxide in this context refers to either absolute or relative amount. Preferably, the amount of oxygen and carbon dioxide being inhaled and exhaled is determined by measuring the end-tidal concentration of oxygen and carbon dioxide and the inspirational concentration of oxygen. However, alternative ways of determining the amounts are feasible as well. Further, the method preferably comprises the step of estimating the base metabolism based on the oxygen and carbon dioxide determination.

"Identify" in this context refers to identification of the presence of any difference, and preferably also a measurement and quantification of the extent of the difference. Further, the identification can comprise a controlled induction of the difference. The identified differences can preferably comprise one or several of:
- a difference in the time period between exhalation and inhalation, such as an apnea period;
- a difference in air volume being inhaled;
- a duration difference between the different phases in the breathing cycles;
- a controlled difference in the dead space volume.

The uptake of oxygen and excretion of carbon dioxide during the breathing cycles are preferably determined based on a quantification of the fluxes of oxygen and carbon dioxide during inhalation and exhalation.

In a preferred embodiment, the invention relates to a method for estimation of the functional residual capacity (FRC) in ventilator treated patients, wherein the difference between the breathing cycles is based on a predetermined breathing pattern of the ventilator equipment.

Hereby, a continuous monitoring of the patient can be performed automatically, and an alarm or alert could e.g. be given when the FRC estimation reaches predetermined critically low values, experiences significant variations and the like. Accordingly, faster and more correct diagnoses can be given. Further, the method can relatively easy be integrated in most ventilator and respirator equipments, since the required measuring means are normally already available, but for other reasons.

Preferably, the estimation of the FRC is used to determine the positive end expiratory pressure (PEEP) for the ventilator equipment.

The invention further relates to a corresponding apparatus for estimation of functional residual capacity (FRC), comprising measuring means for determining the amount of oxygen and carbon dioxide being inhaled and exhaled during at least two breathing cycles, means for identifying at least one difference between said breathing cycles, and processing means for calculation of an estimated FRC based on the measured amount of oxygen and carbon dioxide and said identified difference.

According to another aspect of the invention, it relates to a method for estimation of cardiac output (CO), comprising the steps of determining the amount of oxygen and carbon dioxide being inhaled and exhaled during at least two breathing cycles, identifying at least one difference between said breathing cycles, and estimating the CO based on the determined amount of oxygen and carbon dioxide and said identified difference.

This inventive method is based on the same surprising clinical observation discussed above. The method is very simple and inexpensive to use, since no catheters or the like need to be inserted into the patient. Instead, the estimation is made during relatively normal conditions without causing any risk to the patient. Still, the method has shown to be surprisingly reliable.

Further, the method may be used for relatively continuous monitoring of CO, i.e. where repeated measurements are performed over a time period. This make it possible to use CO measurements for diagnostic and routine control purposes, during rest and exercise, whereby e.g. cardiac deceases can be discovered well before they enter into severe phases.

As in the above, "identify" is in this context means identification of the presence of any difference, and preferably also a measurement and quantification of the extent of the difference. Further, the identification may comprise a controlled induction of the difference. The identified differences may preferably comprise one or several of:
- a difference in the time period between exhalation and inhalation, such as an apnea period.
- a difference in the air volume being inhaled.
- a duration difference between the different phases in the breathing cycles.
- a controlled difference in the dead space volume.

The uptake of oxygen and excretion of carbon dioxide during the breathing cycles are preferably determined based on a quantification of the fluxes of oxygen and carbon dioxide during inhalation and exhalation.

The invention also relates to a corresponding apparatus for estimation of cardiac output (CO) comprising means for determining the amount of oxygen and carbon dioxide being inhaled and exhaled during at least two breathing cycles, means for identifying at least one difference between said breathing cycles, and processing means for estimating the CO based on the determined uptake of oxygen and excretion of carbon dioxide and the identified difference.

In case of ventilator treated patients, a continuous monitoring of the patient can be performed automatically, and an alarm or alert can e.g. be given when the Co estimation reaches predetermined critically low values, experiences significant variations and the like. Accordingly, faster and more correct diagnoses can be given. Further, the method/apparatus can relatively easy be integrated in most ventilator and ventilator equipment, since the required measuring means are normally already available, but for other reasons.

Most preferably, CO and FRC are determined simultaneously, and with at least partly the same equipment.

To summarize, the basic principle of the invention is to accomplish a change in the ventilatory pattern of known magnitude and measure the concomitant changes in FRC~alveolar~end-tidal oxygen and carbon dioxide concentrations. The change in ventilatory pattern can be a short apnea, but can also be accomplished by giving a larger breath of known volume than the preceding breaths, or a smaller breath of known volume than the preceeding breaths. These changes in ventilatory pattern will cause a change of the FRC oxygen and carbon dioxide concentrations that are the basis of the calculation of the FRC volume as well as the cardiac output. In reality, any well defined change in the breathing pattern that causes a measurable change in FRC oxygen and carbon dioxide concentrations can be used for calculation of the volume of FRC and cardiac output. Further, a change in breathing pattern to change gas concentrations can be followed by a compensatory change in opposite direction to re-establish a rapid steady state to enable a new measurement with a minimal delay. Thus, after an apnea a breath with double normal volume can be used or if a large breath is used primarily, this can be followed by a small breath and vice versa. The effect on gas concentrations of the compensatory breath may be utilised to further improve calculations of FRC and cardiac output.

BRIEF DESCRIPTION OF THE DRAWINGS

The invention will now be described in closer detail in the following with reference to preferred embodiments thereof illustrated in the attached drawings, wherein.

Figure 1:
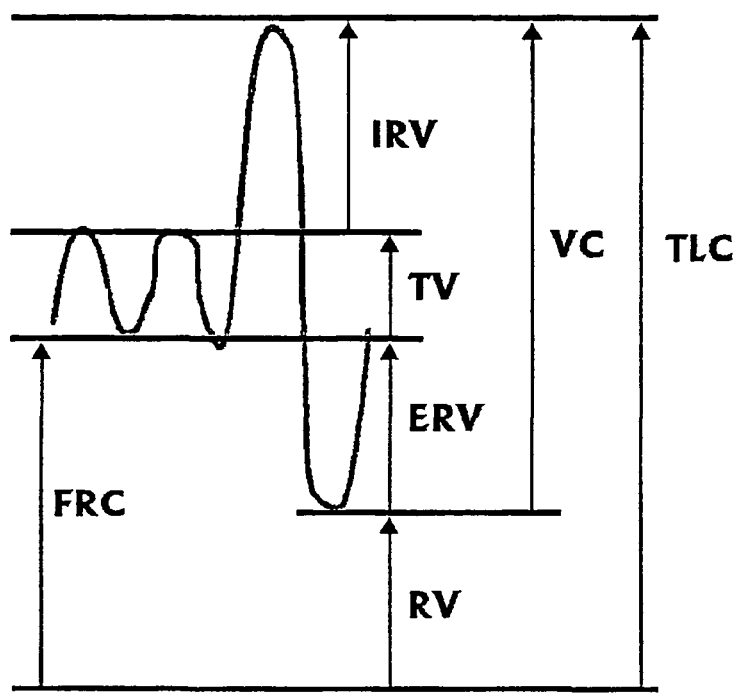
FIG. 1 is an illustration of the changes in volume (on the vertical axis) against time (on the horizontal axis) as an individual breathes.

It should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF A PREFERRED EMBODIMENT OF THE INVENTION

FRC

The method for FRC estimation and FRC monitoring of the invention is based on the clinical observation that patients with small FRC and high oxygen consumption desaturate rapidly compared to "normal" patients. As a consequence changes in gas exchange parameters during different consecutive breathing cycles, such as during a defined apnea, can be used for determination of FRC.

The principle of the present invention is calculation of FRC based on a measured decrease in end-tidal~alveolar~oxygen concentration due to a known wash out of oxygen from the FRC during a short apnea (or other change of the ventilation pattern); i.e. the washed in volume of oxygen divided by the oxygen concentration difference gives the FRC volume. This is only valid if the FRC is not changing volume during the apnea. In this case the FRC is actually decreasing in volume with a volume equivalent to the washed out volume of oxygen. However, during the apnea there is also a wash in to the FRC of carbon dioxide that will counteract the decrease of the FRC volume caused by the wash out of oxygen. The wash in volume of carbon dioxide is dependent on the metabolic production of carbon dioxide, the volume of FRC and the amount of blood perfusing the FRC during the apnea, i.e the cardiac output. Thus, the decrease in oxygen concentration in the FRC during the apnea is dependent on the metabolic uptake of oxygen from the FRC, which will be washed out of the FRC during the apnea, the volume of the FRC, the metabolic production of carbon dioxide which partly will be washed into the FRC during the apnea and partly remain in the lung capillary blood and pass over to the left heart without being washed out into the FRC. The latter part of the metabolically produced carbon dioxide, the lung capillary blood carbon dioxide, $LCBCO_2$, is dependent on the cardiac output and the increase in carbon dioxide concentration of the FRC during the apnea, which is dependent on the volume of the FRC.

Calculating the FRC from oxygen concentration changes during an apnea requires the measurement of the metabolic uptake of oxygen, the calculation of LCBCO2, which requires the measurement of metabolically produced carbon dioxide. Thus, a prerequisite of the invention is the simultaneous measurements of oxygen and carbon dioxide metabolic fluxes and concentration changes during the apnea as the behaviour of oxygen and carbon dioxide is dependent on each other as well as the volume of FRC and the cardiac output.

The amount of oxygen and carbon dioxide inhaled and exhaled by the patient is determined during at least two breathing cycles, wherein there exist at least one difference between said breathing cycles. The difference comprises one or several of the following:

- a difference in the time period between exhalation and inhalation. For example, one of the breathing cycles could comprise an apnea period. Such an apnea could preferably have a duration of 5-25 seconds, and most preferably 8-15 seconds.
- a difference in air volume being inhaled.
- a duration difference between the different phases in the breathing cycles.

The amount of oxygen and carbon dioxide inhaled and exhaled during the breathing cycles is being determined based on a quantification of the fluxes of oxygen and carbon dioxide during inhalation and exhalation. Preferably, the estimation is based on a measurement of the end-tidal concentration of oxygen and carbon dioxide and the inspirational concentration of oxygen.

More specifically, the effect of oxygen uptake from alveoli to blood on the end-tidal concentration of $O_2$ and the inflow of $CO_2$ to the alveoli on end-tidal $CO_2$ concentration, i.e. $O_2$- and $CO_2$-concentrations of FRC, after an apnea can be determined. Oxygen consumption, $VO_2$, and carbon dioxide production $VCO_2$, can be measured by indirect calorimetry, as is known in the art. The inspiratory and expiratory alveolar tidal volumes, $TV_{AI}$ and $TV_{AE}$, can be calculated by Bohr's formula and Haldane transformation, as disclosed in Holk K, Einarsson S G, Svensson K L, Bengtsson J-P, Stenqvist O (1996): "Continuous non-invasive monitoring of energy expenditure, oxygen consumption and alveolar ventilation during controlled ventilation: Validation in an oxygen consuming lung model", Acta Anaesthesiol Scand 40:1-8.

Figure 3:
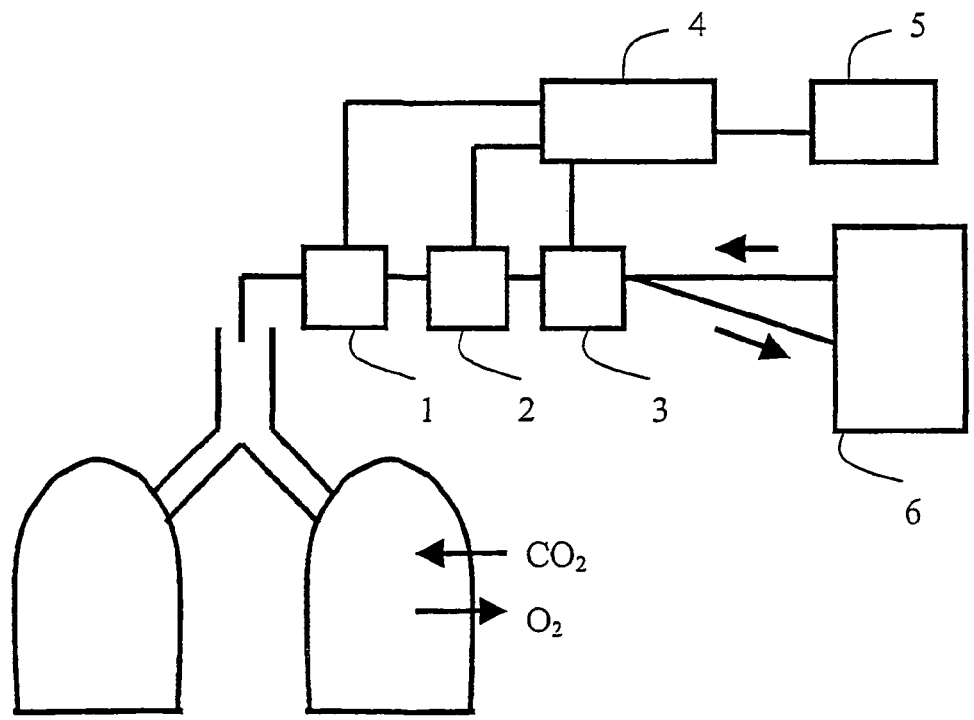
FIG. 3 is a schematic illustration of an apparatus according to an embodiment of the invention.

An apparatus for measuring FRC according to an embodiment of the invention is schematically illustrated in FIG. 3. The apparatus comprises measuring means 1 for measuring the flux of carbon dioxide into and out from the lungs, measuring means 2 for measuring the flux of oxygen into and out from the lungs, and measuring means 3 for identifying and measuring differences between breathing cycles. The measuring means 3 can also be used for inducing such differences, as is discussed in the following. The measuring means 1-3 are connected to processing means 4, such as microprocessor, a personal computer or the like, for calculation of the FRC value based on the input measurement values. The resulting FRC estimation is be forwarded to output means 5, such as a printer, a terminal, a display, an alarm device, a speaker or the like.

The respiration can also be controlled by a respirator or ventilation equipment 6. One or several of the measuring means 1-3, the processing means 4 and the output means 5 may further be integrated with the ventilation equipment 6.

Figure 4:
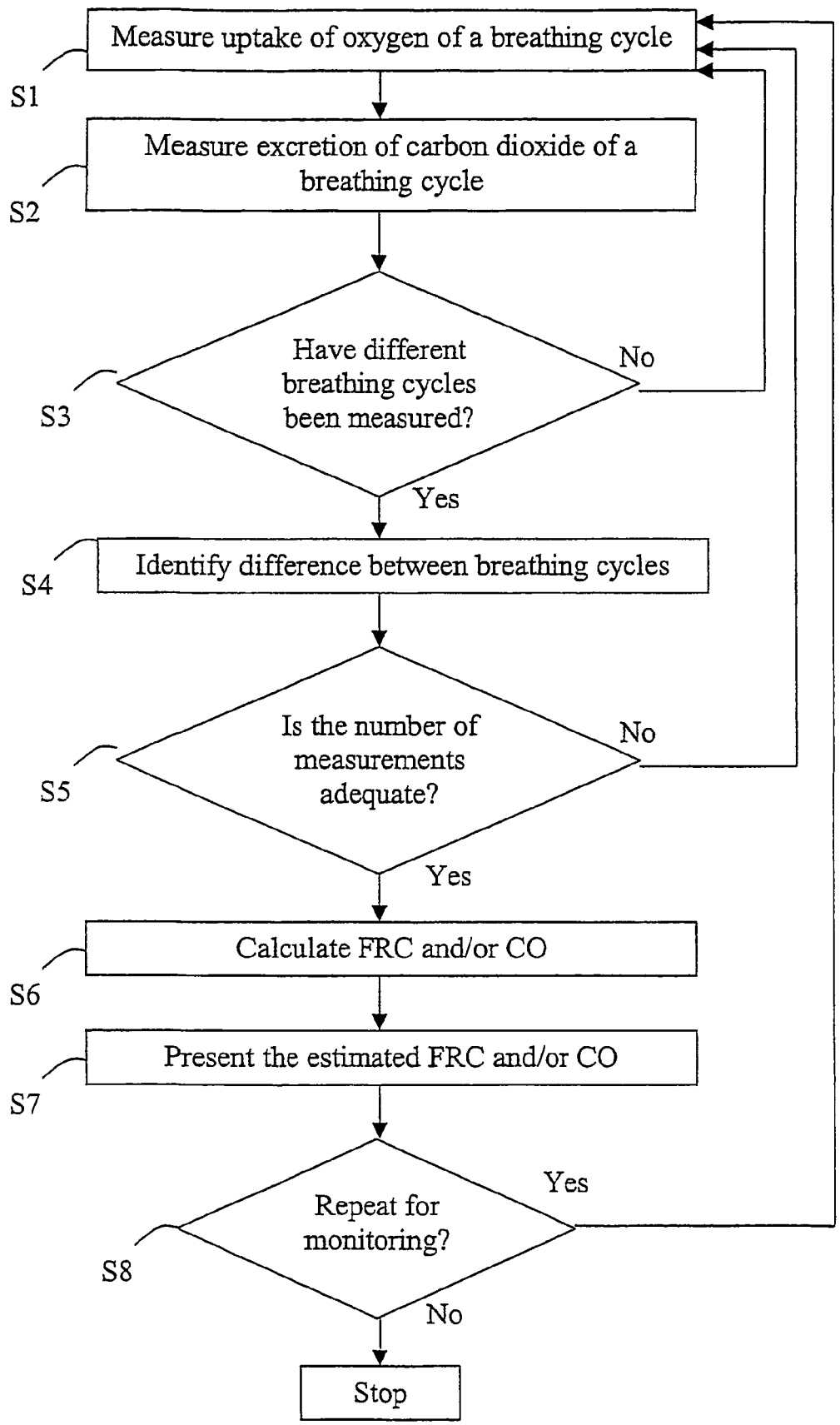
FIG. 4 is a schematic illustration of a method according to an embodiment of the invention.

According to one preferred embodiment, the method of the invention generally comprises the steps as indicated in FIG. 4. In the first steps S1, S2 the uptake of oxygen and excretion of carbon dioxide during a breathing cycle are measured. This is repeated for an adequate number of breathing cycles, so that at least two breathing cycles with a difference have been measured, step S3. Thereafter, the difference between the breathing cycles is identified, step S5. If several measuring processes are performed in order to obtain an average value, the first steps S1-S4 are repeated, step S5.

Thereafter, based on the measured oxygen uptake, the measured carbon dioxide excretion and the identified difference, the FRC is calculated, step S6. The estimated FRC value is to be presented to the user through an output device, such as a printer, a terminal or the like. It is also possible to present the result by using an alarm or the like to indicate dangerous, abnormal or exceptional values.

If the measuring process is repeated for continuous monitoring, the steps S1-S7 are then repeated, step S8.

Figure 2A:
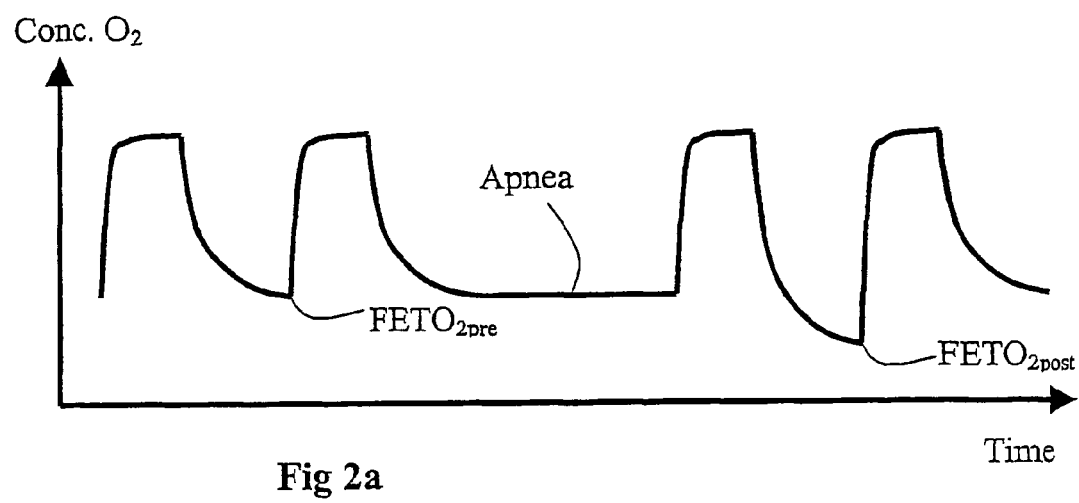
FIG. 2a is a schematic illustration of the changes in tidal $O_2$ fraction over consecutive respiration cycles.
Figure 2B:
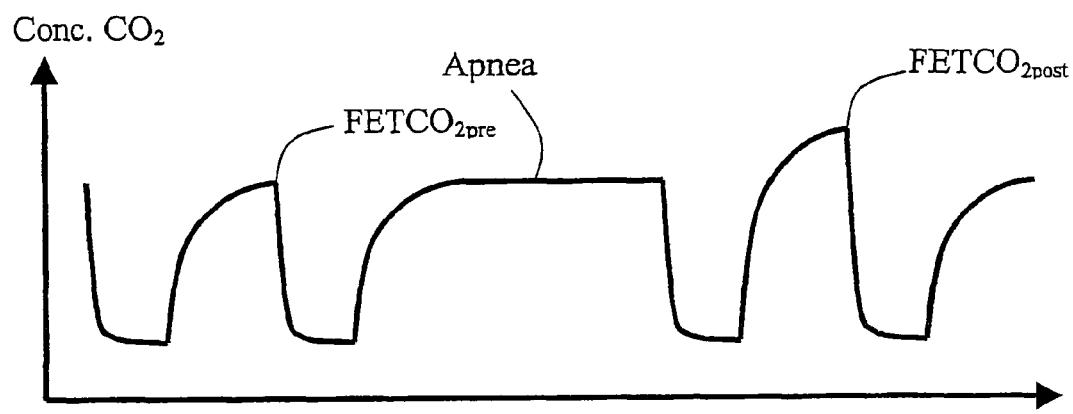
FIG. 2b is a schematic illustration of the changes in tidal $CO_2$ fraction over consecutive respiration cycles.

According to another preferred embodiment of the invention wherein the difference between the breathing cycles is constituted by an added apnea, the following steps were performed:

1. End tidal $O_2$ and $CO_2$ fractions before the apnea, $FETO_{2pre}$ and $FETCO_{2pre}$ were determined. The tidal fractions of $O_2$ typically vary as illustrated in FIG. 2a. The $O_2$ fraction typically increases to about 40% during inhalation, and then decreases to about 35% during exhalation. The end tidal value $FETO_{2pre}$ is the fraction right before an inhalation. The tidal fractions of $CO_2$ typically vary correspondingly, as is illustrated in FIG. 2b. The $Co_2$ fraction typically decreases to about 0% during inhalation, and then increases to about 4-5% during exhalation. The end tidal value $FETCO_{2pre}$ is the fraction right before an inhalation.

2. Thereafter, an expiratory hold, i.e. an apnea, was established for 8-15 seconds, as is likewise illustrated in FIGS. 2a and 2b.

3. The amount of $O_2$ taken up from the alveoli during apnea, $VO_{2\,apnea}$ and the amount of $CO_2$ excreted into the alveoli, $VCO_{2\,apnea}$ can be calculated as the product of apnea time fraction, $Ft_{apnea}$ and the $VO_2$ and $VCO_2$ respectively. The $VCO_{2\,apnea}$ is reduced by the amount dissolved in lung capillary blood (LCB) due to the increase in $PCO_2$ caused by the apnea.

4. End-tidal $O_2$ and $CO_2$ fractions, $FETO_{2post}$ and $FETCO_{2post}$ of the first post-apnea exhalation were then measured, as is illustrated in FIGS. 2a and 2b.

Then, the following calculations are being performed: End-tidal $O_2$- and $CO_2$-fraction before the apnea is be expressed as:

$$FETO_{2pre} = \frac{VO_{2pre}}{FRC} \quad (1)$$

$$FETCO_{2pre} = \frac{VCO_{2pre}}{FRC} \quad (2)$$

where the $VO_2$ and $VCO_2$ are the volumes of $O_2$ and $CO_2$ in the FRC before the apnea.

End-tidal $O_2$- and $CO_2$-fraction after the apnea is being expressed as:

$$FETO_{2post} = \frac{VO_{2pre} + TV_{AI} \times FIO_2 - \dot{V}O_{2apne}}{FRC + TV_{AE} - LCBCO_2} \quad (3)$$

$$FETCO_{2post} = \frac{VCO_{2pre} + \dot{V}CO_{2apne} - LCBCO_2}{FRC + TV_{AE} - LCBCO_2} \quad (4)$$

where the $LBCCO_2$ is the part of the $VCO_2$ that will remain in the pulmonary capillary blood during the apnea as a result of the increase in alveolar/pulmonary capillary $CO_2$-tension and where the $VO_2$ and $VCO_2$ are the volumes of $O_2$ and $CO_2$ in the FRC before the apnea.

FRC can then be expressed as:

$$FRC = \frac{(FETCO_{2post} - 1)(TV_{AI} \times FIO_2 - \dot{V}O_{2apne}) + FETO_{2post}(TV_{AE} - \dot{V}CO_{2apne})}{FETO_{2post}(FETCO_{2pre} - 1) + FETO_{2pre}(1 - FETCO_{2post})}$$

A person skilled in the art will appreciate that similar calculations could be made for other types of differences, etc.

Verification of FRC Measurement

In order to test the above described FRC measurement a lung model FRC measurement was performed. A lung model with $CO_2$ output and $O_2$ consumption, achieved by combustion of hydrogen, was used. FRC was changed between 1.6 and 3.1 liters by addition of volume to the single alveolus, which was also the combustion chamber. The reference value of FRC was obtained by five repeated measurements by injection of a known amount of $CO_2$ into the lung model.

The lung model was ventilated with a Siemens Servo 900C and $CO_2$, $O_2$ and ventilation volumes were analysed using a Datex-Ohmeda AS/3 gas/spirometry module. Fifty FRC measurements were performed with apnea times 8-15 seconds, minute ventilation 10 and 12 L/min, respiratory rate 15, and $VCO_2/VO_2$ of 200/200 and 200/240 mL/min.

Further, repeated apneas were performed in two patients on volume controlled ventilation at PEEP 10, 3 and 10 cm $H_2O$, five-six apneas at each setting. FRC was calculated from gas exchange parameters averaged over three consecutive apneas. The increase in expired tidal volume was measured during PEEP release from 10 to 3 cm $H_2O$.

Figure 5:
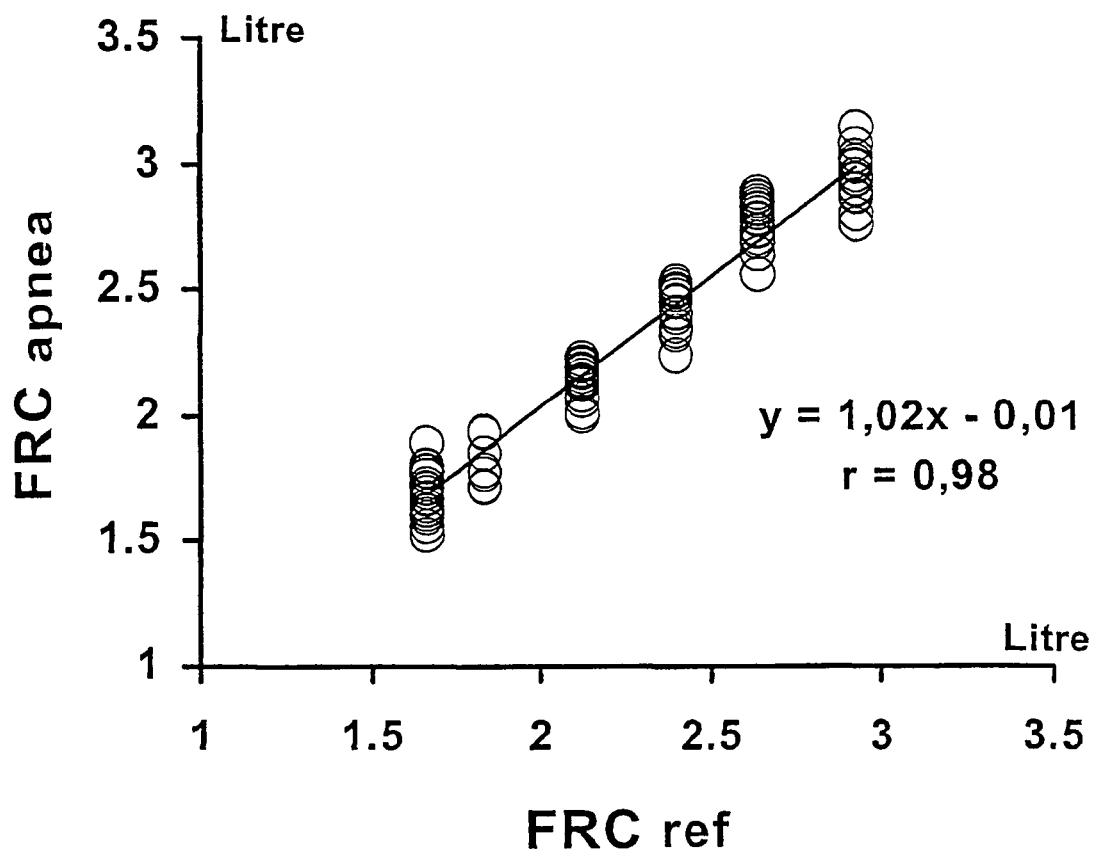
FIG. 5 is a diagram illustrating the correlation between $FRC_{apnea}$ measured in a lung model with the apnea method and $FRC_{ref}^{apnea}$ measured by conventional gas dilution technique.

There was a very good correlation (r=0.98) and agreement between the FRC measured with the apnea method and reference FRC in the lung model with a bias of 34 ml and limits of agreement (±2SD) 160 and −230 mL respectively, as is illustrated in FIG. 5.

Figure 6:
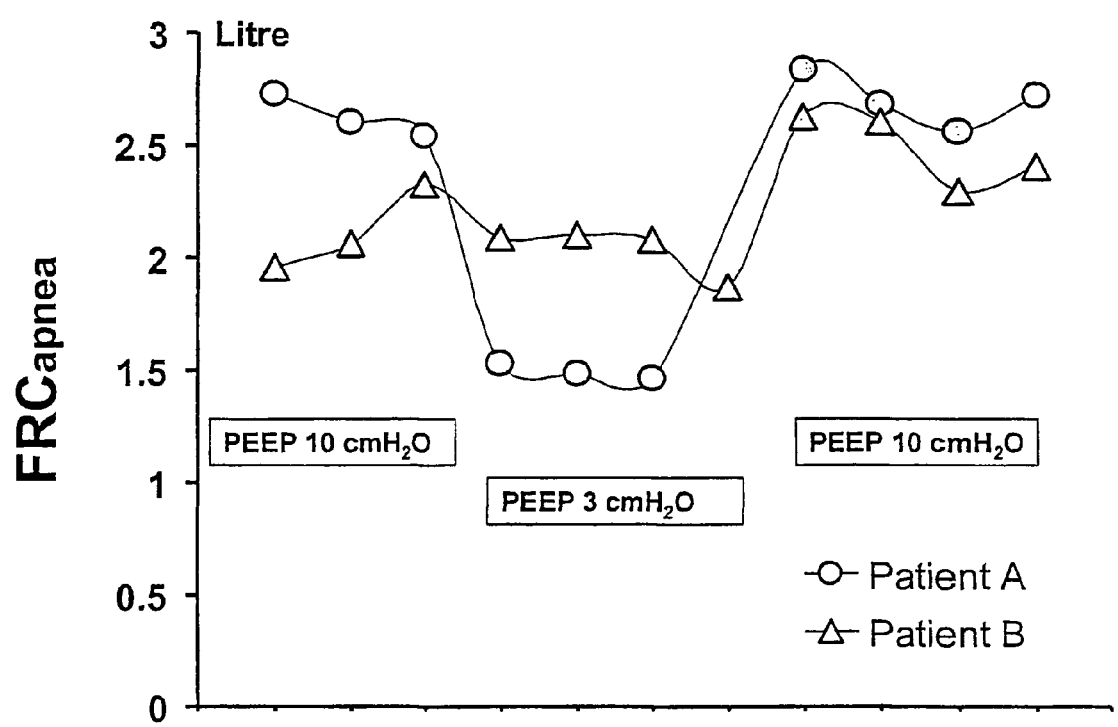
FIG. 6 is a diagram illustrating repeated $FRC_{apnea}$ measurements in two patients, A and B, with PEEP 10, 3 and 10 cm $H_2O$. Each $FRC_{apnea}$ value was based on measurements from three consecutive updated apneas.

Increase in tidal volume during PEEP release in the patients from 10 to 3 cm $H_2O$ was 901 and 608 ml in patient A and B respectively indicating a corresponding change in FRC. FRC measurements at different PEEP levels are shown in FIG. 6. Apparently the decrease in FRC due to PEEP release can be detected with this new method.

As demonstrated above quantification of $O_2/CO_2$ fluxes during a short apnea or other types of differences between different breathing cycles can be used for measurements of FRC. The major advantage of the methodology is that it relies on uptake of $O_2$ and excretion of $CO_2$ and that clinically available monitors like a spirometer, a fast response capnograph and oxymeter are the only instruments necessary.

We assume that the $O_2/CO_2$ flux during the apnea period is distributed as during normal breathing, resulting in an end-tidal $O_2$- and $CO_2$-concentration after the apnea, representative of the whole FRC. The influence of alveolar dead space is proportionally the same on pre- and postapnea end-tidal $O_2/CO_2$ concentrations.

The outflow $O_2$ (oxygen uptake) from the alveoli is unaffected by the apnea period, as the oxygen dissociation curve is very flat at levels of oxygen tensions present in the pulmonary capillaries. The volume change of FRC during the apnea is equal to the difference in $VO_2$ and $VCO_2$ which causes a slightly lowered expired tidal volume. However, the increased solubility of $CO_2$ in blood when increasing the partial pressure during apnea, leads to more $CO_2$ being dissolved in pulmonary capillary blood. The amount of $CO_2$ remaining in blood is dependent on the increase in $PCO_2$ and cardiac output. Thus, the true expiratory alveolar tidal volume after the apnea will be considerably smaller than accounted for by difference in oxygen consumption and carbon dioxide production. The apnea period will change the $O_2/CO_2$ concentrations for a short period. It can be estimated that a new steady state is established within 1-3 minutes. Accordingly, a ventilator can be programmed to perform a short apnea as often as every third minute, monitoring FRC 20 times/h.

The FRC measurement according to the invention provides a simple method for monitoring FRC in ventilator treated patients based on gas exchange measurements during a short apnea. This technique provides the clinician and the researcher with a useful tool for continuous monitoring of lung volume during the development of acute lung injury and to assess the effect of different ventilatory strategies such as the "open lung concept".

However, the invention can also be used for other types of differences than apneas, and can also be used for patients with spontaneous respiration. In that case, the patient voluntarily holding his breath, taking a deeper breath or the like could provide the difference.

Further, in order to improve the reliability of the estimation of the FRC, several measurements can be carried out, the estimation being determined as an average value of said measurements.

Not all the air that passes into the respiratory tract reaches the alveoli. Even in normal individuals, about one third of a tidal volume is wasted in the anatomical dead space. Dead space may be:

Apparatus dead space;
Anatomical dead space (related to the volume of the conducting passages);
Alveolar dead space (related to alveoli that are well ventilated but poorly perfused, so they effectively contribute to the dead space).

The physiological dead space is the sum of the anatomical and alveolar dead spaces, and represents all components of the tidal volume that do not take part in gas exchange.

FRC can alternatively be calculated based on the partial rebreathing method for determination of cardiac output, where an increase in endtidal $CO_2$ tension is achieved by increasing the dead space during a limited period—long enough to reach a steady state and short enough to avoid recirculation of $CO_2$ in mixed venous blood. This period is typically 20-60 seconds. During the first period after increasing dead space, the rate of rise of the end-tidal $CO_2$ tension is dependent on the volume of the FRC and the amount of $CO_2$ dissolved in blood as a result of the rise in endtidal $CO_2$ tension. The rise in endtidal $CO_2$ is measured breath-by-breath and the amount of $CO_2$ dissolved in blood during the initial period after insertion of an extra dead space can be calculated from the difference in $VCO_2$ and the difference in endtidal $CO_2$ with and without extra dead space. These values can be entered into formula 2 and 4 of the description of the apnea method for determination of FRC and will give the value for FRC.

Cardiac Output

The method according to the invention for determining cardiac output (co) uses Fick's equation for carbon dioxide and measurements of the functional residual capacity, FRC, by quantifying oxygen/carbon dioxide fluxes during e.g. a short apnea.

The principle of the present investigation is to calculate the lung capillary perfusion~cardiac output based on measured changes in end-tidal~alveolar~FRC carbon dioxide concentration as a result of a short apnea (or other change in ventilatory pattern). The increase in end-tidal carbon dioxide concentration is dependent on the metabolic output of carbon dioxide, how much of the metabollically produced carbon dioxide that will remain in lung capillary blood as a result of the increase in FRC carbon dioxide concentration which is dependent on the cardiac output and the volume of the FRC. The metabolic output of carbon dioxide prior to the apnea is easily measured with conventional indirect calorimetric methodology. The volume of FRC can be calculated based on a measured decrease in end-tidal-alveolar-oxygen concentration due to a known wash out of oxygen from the FRC during the apnea (or other change of the ventilation pattern) i.e. the washed in volume of oxygen divided by the oxygen concentration difference gives the FRC volume. This is only valid if the FRC is not changing volume during the apnea. In this case the FRC is actually decreasing in volume with a volume equivalent to the washed out volume of oxygen. However, during the apnea the wash in to the FRC of carbon dioxide will counteract the decrease of the FRC volume caused by the wash out of oxygen. The wash in volume of carbon dioxide is dependent on the metabolic production of carbon dioxide, the volume of FRC and the amount of blood perfusing the FRC during the apnea, i.e the cardiac output. Thus, the decrease in oxygen concentration in the FRC during the apnea is dependent on the metabolic uptake of oxygen from the FRC, which will be washed out of the FRC during the apnea, the volume of the FRC, the metabolic production of carbon dioxide which partly will be washed into the FRC during the apnea and partly remain in the lung capillary blood and pass over to the left heart without being washed out into the FRC. The latter part of the metabolically produced carbon dioxide, $LCBCO_2$, is dependent on the cardiac output and the increase in carbon dioxide concentration of the FRC during the apnea, which is dependent on the volume of the FRC.

Calculating the cardiac output from carbon dioxide concentration changes during an apnea requires the measurement of metabolical uptake of oxygen, the calculation of $LCBCO_2$, which requires the measurement of metabolically produced carbon dioxide. Thus, a prerequisite of the invention is the simultaneous measurements of oxygen and carbon dioxide metabolic fluxes and concentration changes during the apnea as the behaviour of oxygen and carbon dioxide is dependent on each other as well as the volume of FRC and the cardiac output.

In the previous a methodology for monitoring of FRC by measurements of oxygen and carbon dioxide fluxes during a short apnea is presented. The base of this methodology is that changes in alveolar carbon dioxide and oxygen concentrations are almost linear during an apnea of short duration. The fall in alveolar oxygen tension is much more pronounced than the rise in alveolar carbon dioxide concentration in spite of the fact that the amounts of the two gases that are metabolically exchanged are rather similar. This phenomenon is related to the contrasting form of the oxygen and carbon dioxide dissociation curves. At the partial pressure of oxygen present in lung capillary blood the dissociation curve is almost horizontal, i.e. the change in oxygen content of blood when changing the alveolar partial pressure of oxygen less than 2 kPa is negligible. The only change in content occurs in plasma with an extremely low oxygen solubility coefficient. In contrast, the carbon dioxide dissociation curve shows a clear increase in solubility of carbon dioxide in blood when the partial pressure rises. The increase in solubility amounts to ~25 ml carbon dioxide/kPa/Liter blood. As a side information when calculating the FRC by the apnea method, the amount of carbon dioxide dissolved in blood as a result of the increase in $CO_2$ partial pressure, is determined. Thus, all data necessary for determination of the lung perfusion-cardiac output minus shunt flow (cardiac output perfusing non-ventilated lung) are available:

$\Delta ETCO_2$ mean rise in endtidal $CO_2$ tension during the apnea $LCBCO_2$=amount of $CO_2$ dissolved in blood as a result of the increase in $CO_2$ partial pressure $At$=Apnea time $kCO_2$=$CO_2$ dissociation curve coefficient $$LCBF \text{ (Lung capillary blood flow)}=(LCBCO_2* 60/At)/(\Delta ETCO_2 * kCO_2)$$

The shunt flow is calculated in a two step sequence where the shunt fraction (Fsh) is estimated by using a default value for the arterial—mixed venous oxygen content difference of 50 ml in the standard shunt fraction equation:

$$(CcapO_2-CaO_2)/(CcapO_2-(CaO_2-50))$$

Initial cardiac output (IniCO) is calculated as:

$$LCBF/(1-Fsh)$$

Final cardiac output is determined by a second estimation of the shunt fraction based on a corrected default value for the arterial—mixed venous oxygen content difference, which is calculated from the carbon dioxide production and a default value for the ratio between the carbon dioxide production and the oxygen consumption (RQ) of 0.8 divided by the initial C 0 (IniCO)

The final default value for the arterial—mixed venous oxygen content difference:

$$(VCO_2/0.8)/IniCO$$

The final shunt fraction (finFsh) is calculated as $$(CcapO_2-CaO_2)/(CcapO_2-(CaO_2-(VCO_2/0.8)/IniCO)))$$

The final cardiac output is calculated as $$LCBCO_2/(1-finFsh)$$

The method and apparatus for FRC estimation generally described with reference to FIG. 3 and FIG. 4 above also applies to the method and apparatus for CO estimation. Further, all the features discussed regarding FRC estimation and CO estimation are exchangeable and could be used in either one of the estimations, unless something else is specifically indicated.

Accordingly, quantification of $O_2/CO_2$ fluxes during a short apnea or other types of differences between different breathing cycles can be used for measurements of cardiac output (CO). The major advantage of this method is that it relies on uptake of $O_2$ and excretion of $CO_2$ and that clinically available monitors like a spirometer, a fast response capnograph and oxymeter are the only instruments necessary.

The determination of CO according to the invention provides a simple method for monitoring CO in ventilator treated patients based on gas exchange measurements during a short apnea. This technique provides the clinician and the researcher with a useful tool for continuous monitoring of CO.

However, the invention can also be used for other types of differences than apneas, and can also be used for patients with spontaneous respiration. In that case, the patient is told to voluntarily hold his breath, taking a deeper breath or to perform a breathing pattern providing such difference.

Further, in order to improve the reliability of the CO estimation, several measurements may be carried out in a sequence, whereby the estimation is determined as an average value of said measurements.

The invention claimed is:

1. A method for estimation of functional residual capacity (FRC) in a person, comprising:
    establishing a breathing pattern;
    determining the amount of oxygen and carbon dioxide being inhaled and exhaled during a first breathing cycle comprised by said breathing pattern;
    accomplishing a first change in said breathing pattern of known magnitude;
    determining the amount of oxygen and carbon dioxide being inhaled and exhaled during a second breathing cycle;
    estimating the FRC based on the determined amounts of oxygen and carbon dioxide in said first and second breathing cycles.

2. The method of claim 1, wherein said first change of breathing pattern is selected from apnea, a breath volume larger than the breath volume of said first breathing cycle, a breath volume smaller than the breath volume of said first breathing cycle, a duration difference between the different phases in said first and second breathing cycles, a difference in dead space volume.

3. The method of claim 1, wherein said second breathing cycle is followed by a second change in breathing pattern of known magnitude compensatory to said first change in breathing pattern of known magnitude to re-establish a steady state allowing a new estimation of FRC with minimal delay.

4. The method of claim 3, wherein said first change in breathing pattern is an increase of the time period between exhalation and inhalation or a breath with substantially decreased breath volume and said second change in breathing pattern is a breath with substantially increased breath volume.

5. The method of claim 3, wherein said first change in breathing pattern is a breath with substantially increased breath volume and said second change in breathing pattern is an increase of the time period between inhalation and exhalation or a breath with substantially decreased breath volume.

6. The method of claim 2, comprising an apnea period of from 5 to 25 seconds.

7. The method of claim 6, comprising an apnea period of from 8 to 15 seconds.

8. The method of claim 1, wherein the amount of oxygen and carbon dioxide being inhaled and exhaled is determined by measuring the end-tidal concentration of oxygen and carbon dioxide and the inspirational concentration of oxygen.

9. The method of claim 2, wherein said difference in dead space volume is increased during a limited period of time.

10. The method of claim 9, wherein said period of time is short enough to avoid re-circulation of carbon dioxide in mixed venous blood.

11. The method of claim 1, comprising the determination of oxygen uptake and carbon dioxide excretion during said first breathing cycle based on the determined amount of oxygen and carbon dioxide being inhaled and exhaled.

12. The method of claim 1, wherein the estimation of FRC is repeated for continuous monitoring of FRC.

13. The method of claim 1, wherein the estimation of FRC comprises several of said determinations so as to provide an average FRC estimation.

14. The method of claim 1, wherein said person is a ventilator treated patient and wherein said first change in breathing pattern is based on a predetermined breathing pattern of the ventilator.

15. The method of claim 14, comprising the determination of post expiration end pressure (PEEP) of the ventilator based on FRC.

16. An apparatus for measuring functional residual capacity (FRC), comprising:
    means for establishing a breathing pattern;
    means for determining the amount of oxygen and carbon dioxide being inhaled and exhaled during a first breathing cycle comprised by said breathing pattern;
    means for accomplishing a first change in said breathing pattern of known magnitude;
    means for determining the amount of oxygen and carbon dioxide being inhaled and exhaled during a second breathing cycle;
    means for estimating the FRC based on the determined amounts of oxygen and carbon dioxide in said first and second breathing cycles.

17. The apparatus of claim 16, wherein said means for estimating FRC are capable of estimating the base metabolism from said determination of oxygen and carbon dioxide.

18. The apparatus of claim 17, wherein said first change of breathing pattern is selected from apnea, a breath volume larger than the breath volume of said first breathing cycle, a breath volume smaller than the breath volume of said first breathing cycle, a duration difference between the different phases in said first and second breathing cycles, a difference in dead space volume.

19. The apparatus of claim 16, comprising means for accomplishing a second change in breathing pattern of known magnitude after completion of said second breathing cycle, the means for accomplishing said second change being compensatory to the means for accomplishing said first change in breathing pattern and being capable of re-establishing a steady state allowing a new estimation of FRC with minimal delay.

20. The apparatus of claim 19, wherein said first change in breathing pattern is an increase of the time period between exhalation and inhalation or a breath with substantially decreased breath volume and said second change in breathing pattern is a breath with substantially increased breath volume.

21. The apparatus of claim 19, wherein said first change in breathing pattern is a breath with substantially increased breath volume and said second change in breathing pattern is an increase of the time period between inhalation and exhalation or a breath with substantially decreased breath volume.

22. The apparatus of claim 20, comprising an apnea period of from 5 to 25 seconds.

23. The apparatus of claim 22, comprising an apnea period of from 8 to 15 seconds.

24. The apparatus of claim 16, wherein the amount of oxygen and carbon dioxide being inhaled and exhaled is determined by measuring the end-tidal concentration of oxygen and carbon dioxide and the inspirational concentration of oxygen.

25. The apparatus of claim 16, wherein the estimation of FRC is repeated for continuous monitoring of FRC.

26. The apparatus of claim 16, wherein the estimation of FRC comprises several of said determinations so as to provide an average FRC estimation.

27. The apparatus claim 16, wherein said first change in breathing pattern is based on a predetermined breathing pattern of the ventilator.

28. The apparatus of claim 16, comprising means for the determination of post expiration end pressure.

29. The apparatus of claim 18, wherein said difference in dead space volume is increased during a limited period of time.

30. A method for estimation of functional residual capacity (FRC), comprising the steps of determining the amount of oxygen and carbon dioxide being inhaled and exhaled during at least two breathing cycles, identifying at least one difference between said breathing cycles, and estimating the FRC based on the determined amount of oxygen and carbon dioxide and said identified difference.

31. A method according to claim 30, further comprising the step of estimating the base metabolism from the oxygen and carbon dioxide determination.

32. A method according to claim 30, wherein the amount of oxygen and carbon dioxide being inhaled and exhaled is determined by measuring the end-tidal concentration of oxygen and carbon dioxide and the inspirational concentration of oxygen.

33. A method according to claim 30, wherein the difference between the breathing cycles comprises a difference in the time period between exhalation and inhalation.

34. A method according to claim 33, wherein one of the breathing cycles comprises an apnea period, preferably having a duration of 5-25 seconds, and most preferably 8-15 seconds.

35. A method according to claim 30, wherein the difference between the breathing cycles comprises a difference in air volume being inhaled.

36. A method according to claim 30, wherein the difference between the breathing cycles comprises a duration difference between the different phases in the breathing cycles.

37. A method according to claim 30, wherein the difference between the breathing cycles comprises a controlled difference in the dead space volume.

38. A method according to claim 37, wherein the dead space is increased during a limited period, said time period preferably being long enough to reach a steady state and short enough to avoid recirculation of $CO_2$ in mixed venous blood.

39. A method according to claim 30, wherein the determined amount of oxygen and carbon dioxide being inhaled and exhaled is used to determine the uptake of oxygen and excretion of carbon dioxide during the breathing cycles.

40. A method according to claim 30, wherein the estimation of the FRC is repeated for continuous monitoring of the FRC.

41. A method according to claim 30, wherein the estimation of the FRC comprises several measurements, whereby the estimation is determined as an average value of said measurements.

42. A method for estimation of functional residual capacity (FRC) in ventilator treated patients according to claim 30, wherein the difference between the breathing cycles is based on a predetermined breathing pattern of the ventilator equipment.

43. A method according to claim 42, wherein the estimation of the FRC is used to determine the post expiration end pressure (PEEP) for the ventilator equipment.

44. An apparatus for estimation of functional residual capacity (FRC), comprising measuring means for determining the amount of oxygen and carbon dioxide being inhaled and exhaled during at least two breathing cycles, means for identifying at least one difference between said breathing cycles, and processing means for calculation of an estimated FRC based on the measured amount of oxygen and carbon dioxide and said identified difference.

45. An apparatus according to claim 44, wherein the processing means further being adapted to estimate the base metabolism from the oxygen and carbon dioxide determination.

46. An apparatus according to claim 44, wherein the means for determining the amount of oxygen and carbon dioxide being inhaled and exhaled comprises means for measuring the end-tidal concentration of oxygen and carbon dioxide and the inspirational concentration of oxygen.

47. An apparatus according to claim 44, wherein the difference between the breathing cycles comprises a difference in the time period between exhalation and inhalation.

48. An apparatus according to claim 47, wherein one of the breathing cycles comprises an apnea period, preferably having a duration of 5-25 seconds, and most preferably 8-15 seconds.

49. An apparatus according to claim 44, wherein the difference between the breathing cycles comprises a difference in air volume being inhaled.

50. An apparatus according to claim 44, wherein the difference between the breathing cycles comprises a duration difference between the different phases in the breathing cycles.

51. An apparatus according to claim 44, wherein the means for measuring the uptake of oxygen and excretion of carbon dioxide during the breathing cycles comprises means for determining the fluxes of oxygen and carbon dioxide during inhalation and exhalation.

52. An apparatus for estimation of functional residual capacity (FRC) in ventilator treated patients according to claim 44, wherein the difference between the breathing cycles is based on a predetermined breathing pattern of the ventilator equipment.

* * * * *